United States Patent [19]

Pargeter et al.

[11] 4,196,100

[45] Apr. 1, 1980

[54] CATALYST USEFUL FOR METHANATION AND PREPARATION THEREOF

[75] Inventors: John K. Pargeter, Warwick; Umar M. U. Ahmad, Middletown, both of N.Y.

[73] Assignee: The International Nickel Co., Inc., New York, N.Y.

[21] Appl. No.: 868,406

[22] Filed: Jan. 10, 1978

[51] Int. Cl.$^2$ .................... B01J 27/02; B01J 23/70
[52] U.S. Cl. ................... 252/439; 252/461
[58] Field of Search ................... 252/439, 461

[56] References Cited

U.S. PATENT DOCUMENTS

| | | | |
|---|---|---|---|
| 1,908,286 | 5/1933 | Dorrer | 252/439 |
| 2,295,653 | 9/1942 | Griffith et al. | 252/439 |
| 2,455,713 | 12/1948 | Voorhies | 252/439 |
| 2,511,453 | 6/1950 | Barry | 252/439 |
| 2,512,570 | 6/1950 | Sartor | 252/439 X |
| 2,780,584 | 2/1957 | Doumani | 252/439 X |
| 3,094,409 | 6/1963 | Renzoni et al. | 75/9 |
| 3,274,122 | 9/1966 | Holmes et al. | 252/439 |
| 3,320,182 | 5/1967 | Taylor et al. | 252/466 |
| 3,415,634 | 12/1968 | Dent et al. | 48/213 |
| 3,511,624 | 5/1970 | Humphries et al. | 48/197 |
| 3,527,839 | 9/1970 | Glockner et al. | 252/439 X |
| 3,866,353 | 2/1975 | Krumm et al. | 48/214 |
| 3,912,775 | 10/1975 | Broecker et al. | 252/455 R X |
| 3,922,148 | 11/1975 | Child | 48/197 R |
| 3,945,944 | 3/1976 | Kang | 252/455 R |
| 3,962,140 | 6/1976 | Alcorn et al. | 252/470 |
| 3,967,936 | 7/1976 | Tajbl et al. | 48/197 R |
| 3,988,262 | 10/1976 | Andersen et al. | 252/466 J |
| 3,988,263 | 10/1976 | Hansford | 252/466 J |
| 4,077,912 | 3/1978 | Dollyj et al. | 252/461 |

FOREIGN PATENT DOCUMENTS 629089  3/1963  Belgium ................... 252/439

Primary Examiner—O. R. Vertiz
Assistant Examiner—William G. Wright
Attorney, Agent, or Firm—M. W. Leff; E. C. MacQueen

[57] ABSTRACT

An unsupported particulate catalyst especially useful for methanation reactions is prepared by a method comprising fluid-bed roasting agglomerates of nickel sulfide to form a particulate precursor material which can be reduced to composite particles consisting essentially of a nickel-oxide core with a then coherent adherent layer of nickel thereon, the reduced particles being characterized at the surface by the presence of microcapillary pores interconnecting with each other and the outer surface of the particles.

45 Claims, 10 Drawing Figures

5A

5B

6A

6B

CATALYST USEFUL FOR METHANATION AND PREPARATION THEREOF

This invention relates to a nickel catalyst and its preparation. It is particularly useful for methanation reactions and for reactions carried out in a fluidized-catalyst bed type reactor.

Methanation, i.e., the production of methane by passing hydrogen and oxides of carbon over a catalyst, is a well-known process. It is currently the subject of considerable research as a method for obtaining large supplies of high heating value fuel from fuel gases made from coal.

Several multi-stage processes are being developed for coal gasification. All the processes require a final methanation of a gas mixture including $H_2$ and CO to yield a gas which has a calorific value of at least 800 BTU/scf so as to qualify as a substitute for natural gas. In general, the process gas produced by coal gasification may have a calorific value of about 300–500 BTU/scf, and this is upgraded by steps which include the methanation reaction to form a gas with high BTU's of about 900 to 1000/scf. Between the gasification and methanation step the process gas may be scrubbed to remove acid gases, for example, $H_2S$ and COS, which may be harmful to the methanation catalysts. $CO_2$ may also be removed.

In the above discussion the terms gasification, process gas, synthesis gas, and methanation have been used. The term "gasification" as applied to coal means the conversion of coal in the presence of reacting agents, e.g., steam and oxygen, to produce a gaseous product. The product usually contains CO, $CO_2$, $H_2O$, $H_2$, $CH_4$. Other gases such as higher molecular weight hydrocarbons, $H_2S$, COS may also be present. The higher the percentage of $CH_4$, CO and $H_2$ produced, the more efficient the gasification process is for producing a substitute natural gas. The term "process gas" means the product gas of the gasifications step. The process gas may be used as the feed in a combined shift reaction or it may be further treated, e.g., to remove one or more gases such as $H_2O_{(v)}$ and/or $CO_2$, e.g. in a shift reaction before the final methanation step. The term "synthesis gas" means a gas containing CO, $H_2$ and preferably $CH_4$, which is used as the feed in the final stages of a methanation process. The term "methanation" has already been defined.

Many different methanation processes have been prepared to accommodate the requirements of temperature, pressure and gas feed compositions necessary for a high production of methane. Catalysts are essential to the processes in order to raise the reaction kinetics to practical levels. A major problem is that during the methanation step the reactions are largely exothermic. If not controlled within the reactor the heat generated can cause serious problems such as overheating of the catalyst, with resultant loss of catalyst activity, and/or thermal cracking, with resultant carbon formation—which can foul the catalyst and plug the catalyst bed. In addition, at high temperatures the methanation reaction reverses. Among the many design features proposed to contend with the problem of heat control are: multiple feed inlet arrangements, cooling coils, heat exchange means, and so on. Fluidized catalyst bed have also been used. In a fixed catalyst bed reactor, the catalyst remains stationary and the reactants pass through the bed. In fluidized catalyst beds, the catalyst may remain in the reactor, but it is kept in suspension by a fluidizing medium which may be gas phase or liquid phase.

Proposed processes have been carried out over a wide range of conditions, e.g. in temperatures from about 200° C. to 900° C. and pressures from about 1 to 300 atmospheres. In general, pressures do not affect methane yield until temperatures of about 425° C. are exceeded, and the catalyst bed should be operated at the lowest temperature consistent with catalyst activity and with synthesis gas $H_2$ to CO ratios. At lower $H_2$ to CO ratios it is necessary to use higher pressures. At elevated pressure and/or high feed gas throughputs, the heat production is higher.

It will be appreciated that demands on a catalyst for methanation process are rigorous. As a practical matter they should have good activity at low temperatures, good stability at high temperatures, good selectivity for the production of $CH_4$ without excessive production of $CO_2$. In addition it is highly desirable for the catalysts to be capable of handling a high throughput of the reacting gases ($H_2$ and CO), to be resistant to sulfur poisoning, and to have long life. Moreover, if used in certain types of processes which require a fluidized bed or high pressure, they must also have the physical attributes for such use. It is not surprising, therefore, that considerable research effort has been expended for some time to find satisfactory methanation catalysts.

Nickel catalysts are known to be effective methanation catalysts and both supported and unsupported nickel-containing materials have been used for this purpose. In general, typical catalysts suitable for methanation consist of one or more metals of Group VIII of the Periodic System, or their oxides, supported on or in combination with various refractory metal oxides. For example, it is well known to use nickel or nickel oxide in combination with one or more of alumina, magnesia, thoria, chromia, and with or without additives such as rare earth metals or compounds of alkali or alkaline earth metals. The nickel or nickel oxide with the various combinations of other metals or compounds may be supported on a carrier, e.g. kieselguhr or a refractory material such as alumina, zirconia or silica. Although there have been other types of catalysts reported including those containing a Raney nickel, the general trend has been to prepare the nickel component of the catalyst by precipitation or co-precipitation with other metals or compounds from a solution of a soluble nickel salt - either chemically or thermally. "Co-precipitation", for example, may be carried out by treating an aqueous solution of a nickel salt and an aluminum or a magnesium salt with a base, such as a hydroxide or carbonate of an alkali metal to co-precipitate the Ni and Mg or Al as a hydroxide or carbonate. The co-precipitate can be dried, extruded and reduced under various conditions. If a catalyst supported on a carrier is desired, the mixture of salts may be co-precipitated in the presence of the carrier. Alternatively, a carrier material, e.g. $Al_2O_3$, MgO or $ZrO_2$, in particulate form may be dipped in an aqueous solution of a nickel salt such as nickel nitrate and the solution permitted to impregnate the particles. Thereafter, the impregnated material may be dried and the nickel deposited, e.g., by decomposing the nickel nitrate thermally or by reducing with $H_2$ at an elevated temperature. Examples of U.S. patents which give details on the preparation of nickel catalysts for a variety of methanation processes are:

U.S. Pat. Nos. 3,320,182, No. 3,511,624, No. 3,759,679, No. 3,912,775, No. 3,922,148, No. 3,927,997,

No. 3,928,001, No. 3,933,883, No. 3,945,944, No. 3,950,368, No. 3,962,140, No. 3,988,262, No. 3,988,263, No. 4,002,658, No. 4,005,996.

This list is not intended or purported to exhaust publications in the field of methanation. The list will show, however, the emphasis placed on preparing nickel-type catalysts from nickel precipitated or co-precipitated by one means or another from solution. Some of the nickel catalysts available commercially are supplied in oxide form and must be reduced before use. Others are prereduced and are ready for use. It has been reported that many of the commercially available reduced catalysts are pyrophoric and that unless stabilized after use, used nickel methanation catalysts are pyrophoric so that special precautions must be taken in handling such catalysts in the reduced state before and after use. It is reported also that one of the advantages of using more expensive platinum group metal catalyst is that there is a saving in the cost of reduction or stabilizing equipment on the methanation site on the grounds that the platinum group metals are not pyrophoric.

It is academic in the art of catalysis that the entire history of the preparation of catalysts as well as their compositions are important and often critical. In other words, each step in the preparation is interrelated with other steps and the techniques and conditions used for developing the catalyst at each step are specific to the material at the particular state in its chemical history. At each step in the preparation materials will vary, e.g. chemically, physically and metallurgically. It is known that even very subtle differences in the preparation can have a marked effect on, e.g., activity, selectivity, and stability of a catalyst material. The catalyst proposed heretofore have not been entirely satisfactory and the search has continued for suitable and improved catalysts, which have the optimum properties under process conditions.

In accordance with the present invention a catalyst is provided which is highly active, can handle feed gases, high in hydrogen and carbon monoxide, is more resistant to sulfur poisoning, is stable at high temperatures, and has long life. In addition, the present catalyst is especially adapted for use in a fluidized catalyst bed and for use at relatively high temperatures with high gas throughput. Moreover, the catalysts are nonpyrophoric in their reduced state both before and after use so that no special reduction or stabilizing equipment is required for this purpose.

The invention is more fully described with reference to the accompanying drawings and the description and examples which follow.

INVENTION

Figure 1:
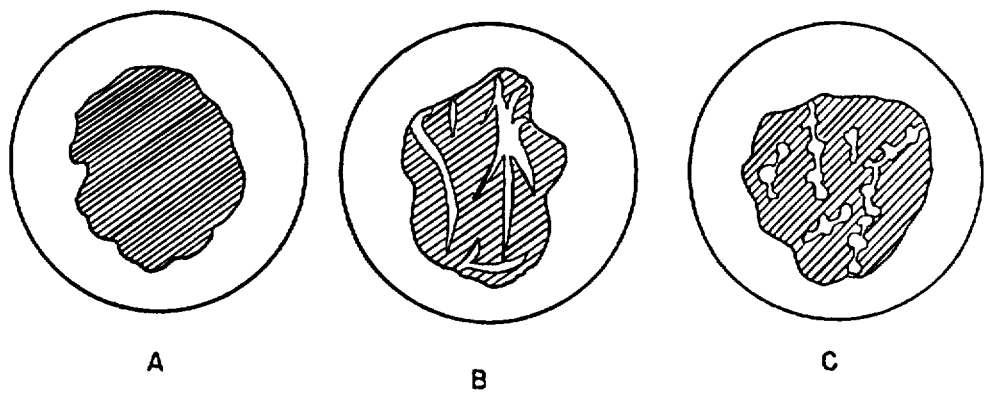
FIGS. 1A, 1B and 1C are a series of drawings illustrating schematically the pore structure of various materials.

In accordance with one aspect of the present invention an unsupported particulate nickel-containing catalyst is provided, said catalyst being composed of, by weight, up to about 13% oxygen, less than about 1% sulfur, and the balance predominantly nickel and having an average particle size of at least about 0.03 mm. with a minimum of fines, said catalyst particles being a composite material consisting essentially of a nickel oxide core and a thin adherent, coherent layer of nickel on said core, the nickel layer being developed under reducing conditions from the nickel oxide core and being characterized by the presence of microcapillary pores interconnecting with each other and with the outer surface of the particles.

Although nickel is the essential catalytic agent of the catalyst of the present invention, the catalytic activity of the material, e.g. for methanation, will be present with considerable dilution of the nickel. For methanation in particular, preferably, the particles will be predominantly nickel, e.g., they will contain greater than 50% nickel, and preferably greater than 75% or even greater than 90% nickel. However, as discussed below, the catalyst materials of the present invention can be tailored for special reactions by incorporating therein various metals or metal compounds.

In accordance with another aspect of the present invention an unsupported particulate precursor catalyst material especially useful in reduced form for methanation reactions comprises nickel oxide and contains at least about 7% oxygen, preferably greater than about 15% oxygen, less than about 1% sulfur and the balance essentially nickel, said catalyst material having a bulk density of less than about 4g/cc, typically about 2.5 to about 3.6 g/cc and an average particle size of at least about 0.03mm. with a minimum of fines, and said precursor catalyst material on being subjected to reducing conditions being converted to a reduced catalyst material having at least a portion at the surface of the nickel oxide reduced to a thin layer of reduced nickel, (i.e. nickel in the elemental state), said reduced nickel being characterized by the presence of microcapillary pores interconnecting with each other and with the outer surface of the particles, and said reduced catalyst material having a superficial surface area of at least about 0.4 m²/g and a pore volume of at least about 0.001 ml/g.

"Fines" means particles having a size less than minus 100 mesh.

The precursor catalyst material may be reduced before use or in the reaction using a reducing medium, which may be the reactants. If reduced prior to use, reduction may be partial or complete. To insure rapid start-up in the reactor and a stabilized reaction pattern it is preferred that the nickel oxide of the precursor catalyst material is at least partially reduced, forming a coherent and adherent coating of nickel on the nickel oxide, said coating being on the average at least about 1/30th of the particle diameter in thickness. From a point of view of economy it is not necessary to prereduce the nickel oxide completely before use in the catalytic process, e.g. methanation. In the methanation process the catalyst will be further reduced.

In accordance with a further aspect of the present invention an unsupported particulate nickel-containing catalyst material is prepared by a process comprising fluid-bed roasting agglomerates comprised of nickel sulfide in an oxidizing atmosphere at a temperature of at least about 600° C., up to about 1500° C., preferably about 1000° C. to about 1300° C. to form a particulate precursor material comprising nickel oxide and containing at least about 7% preferably greater than 15%, e.g. 19–20% oxygen, and the balance essentially nickel. Typically the precursor material comprises nickel oxide and has an average particle size of at least about 0.03 mm., typically about 0.25 to 1.2 mm. with a minimum of fines. In a preferred embodiment the agglomerates are formed from a nickel sulfide powder derived from a nickel matte and the matte contains at least about 7% sulfur, and preferably greater than about 15% sulfur, e.g. about 15 to about 26% sulfur. Preferably, the catalyst which is placed on-stream in the methanation reactor contains a minimum of sulfur, e.g. less than about 0.2%. On-stream, a catalyst with minimum sulfur is preferred since sulfur tends to poison the catalyst, and the lower the initial sulfur content, the greater the life of the catalyst. Preferably, the on-stream catalyst is at least partially reduced.

By fluid-bed roasting is meant a method in which the product is formed in a fluidized bed, e.g. the product particles are formed while held in suspension in an upwardly moving stream of gas.

In a still further aspect of the present invention the nickel oxide-containing precursor catalyst material obtained by fluid-bed roasting agglomerates comprising nickel sulfide is subjected to reducing conditions to convert at least a portion of the nickel oxide at the surface to elemental nickel. To effect reduction, the precursor catalyst material is subjected to a temperature of about 200° C. (390° F.) to about 500° C. (930° F.), preferably from about 300° C. (570° F.)to about 420° C. (790° F.) or 425° C. (800° F.), and more preferably about 315° C. (600° F.) to about 380° C. (715° F.) prior to use in the desired reaction, e.g. methanation, in an atmosphere reducing to nickel oxide for a period of time sufficient to partially reduce the nickel oxide. In one embodiment the precursor catalyst material is reduced prior to use for a sufficient period of time to lower the oxygen content to about 13% or less. In a preferred embodiment the reduction is carried out in a fluidized bed.

The reduction may be carried out in-situ prior to placing the catalyst on-stream. Within the ranges given there is a time-temperature interrelationship. At higher temperatures the treatment time is shorter than at lower temperatures.

The reduced catalyst is characterized by composition and structure of the particles and by internal and surface characteristics on a macro and micro scale. Porosity and pore characteristics of the reduced nickel coating in the interior as well as the outer surface are important for good catalytic activity. Although some shrinkage may occur, in general, the particle size of the precursor material is retained on reduction of the precursor material.

All materials are not alike in regard to either their internal or external structure. Three forms of particles are illustrated schematically in FIGS. 1A, 1B, and 1C. It is quite evident from these particles that there is a significant difference in their structure. FIG. 1C contains microcapillaries interconnected with interior spaces which will enable gas molecules to move into and out readily. On the other hand, FIG. 1A lacks any pores, channels, fissures or cracks and is a compact mass through which the movement of gas molecules will be inhibited. The precursor nickel oxide-containing particles of the present invention have the type of structure illustrated by FIG. 1B, and after reduction in accordance with the present invention they have a surface coating having a microstructure illustrated by the FIG. 1C.

The term "precursor" is applied to the catalyst material prior to reduction, i.e. prior to reduction to form at least the thin layer of elemental nickel on the surface of the catalyst particles, to distinguish it from the reduced catalyst and because in the methanation reaction it is preferred to use the catalyst after it has been at least partially reduced. It has been found that the catalyst is stabilized, i.e. it exhibits better performance, by such reduction prior to use.

As indicated previously, the nickel-containing catalysts of the present invention are especially useful as methanation catalysts. However, they may be used for many other reactions requiring nickel catalysts. The catalyst composition can be tailored to the particular reaction of interest. The catalysts may contain elements of a large number of groups of the Periodic Table. For example, in addition to nickel the catalysts may contain elements or compounds of elements of Groups of the Periodic Table IA, IB, IIA, IIB, IVA, IVB, VB, VIB, VIII, and the rare earth metals. In general, such additional elements may be present in the precursor nickel oxide-containing material, or they may be added by various known techniques to the precursor or reduced catalyst, e.g. by impregnation of a solution of the desired material followed by, e.g., chemical and/or physical deposit of the desired additive from solution, provided the means of addition does not destroy the pore characteristics or other physical attributes of the catalyst materials, which were set forth above.

In general, the nickel oxide-containing precursor particles are comprised of at least about 7% oxygen and the balance essentially nickel. Suitably, the precursor particles may contain about 15% up to about 26% oxygen, and preferably the particles contain above about 20% oxygen. A minimum of about 7% oxygen is required in the precursor on the theory that at least this level of oxygen is needed to produce a catalyst in the reduced state with suitable porosity and microstructure. It is believed that, although some shrinkage may occur, the presence of oxygen and/or a nickel oxide structure in the precursor material provides for the subsequent development of the desired pore volume and pore structure in the reduced catalyst material. The balance of the components may be substantially only nickel. Nickel sulfides from which the nickel oxide precursor particles can be formed typically contain up to about 1% cobalt, up to about 1.5% iron, up to about 3.5% copper, up to about 0.1% platinum group metals, and up to a total of about 2% alkali and/or alkaline earth metals. In general, these metals will carry over into the precursor and the reduced particles.

In a preferred composition the precursor particles contain:
about 7% to about 26% oxygen, e.g. about 23% to 26%,
about 68% to about 93% nickel, e.g. about 72% to 78%,
up to about 1% cobalt, e.g. about 0.5% to 1.5%,
up to about 3.5% copper, e.g. about 0.2% to 1%,
up to about 1.5% iron, e.g. about 0.2% to 0.5%,
up to about 1% sulfur, e.g. about 0.02% to 0.5%.

up to about 1% sulfur, e.g. about 0.02% to 0.5%.

Insofar as the methanation reaction is concerned nickel and cobalt both exhibit catalytic activity, copper appears to increase resistance to poisoning at least up to about 3.5%. Iron is often present as a carry over from the particular ore. The presence of a small amount of sulfur up to about 1%, in the precursor material was found to be beneficial in that it promotes the formation of a suitable pore structure in the reduced nickel. It is contrary to normal catalyst prepration to use the precursor with an intentional sulfur level since sulfur is a poison in the final product.

In general, the precursor materials are in granular form and have an average particle size of at least 0.03 mm. with a minimum of fines, typically the particle size is about 0.25 to about 1.2 mm. (about 16 to about 60 mesh U.S. Sieve Series, preferably about 0.25 to about 0.45 mm. (about 40 to 60 mesh) with a minimum, e.g. less than 1%, of fines. The precursor particles have a surface area (as determined by the BET method) typically of about 0.41 to about 10 m$^2$/g, and a pore volume (as determined by Quantasorb Sorbtion System Test) typically of about 0.001 to about 0.03 ml/g.

In one advantageous method, the particulate precursor catalyst material is prepared by fluid-bed roasting of a nickel sulfide in air or oxygen enriched air. Roasting can be carried out above the softening point of the sulfide but below the melting point of the resultant oxide. The nickel sulfide can be prepared from both sulfidic or oxidic ores, but preferably it is obtained as an intermediate product in the refining of a nickel ore at conditions conducive to forming a suitable catalyst material. This type of intermediate product is known in the art of refining nickel as "nickel oxide sinter". Processes on the extractive metallurgy of nickel ores are described in detail in the literature, e.g. in "The Winning of Nickel", by J. R. Boldt, Jr., Van Nostrand, 1967, and a fluid-bed roasting technique is described on pages 284-286. U.S. Pat. No. 3,094,409 also describes in detail a method for obtaining from nickel sulfides granular nickel oxide sinter particles containing less than 2% and even less than 0.2% sulfur. In particular, U.S. Pat. No. 3,094,409 describes a process for treating finely divided nickel sulfide material containing more than 15% sulfur and obtained from mattes and matte flotation products for the formation of a granular nickel oxide product, which comprises agglomerating the nickel sulfide material with water to form granules with a particle size of between about 65 mesh and about 0.5 inch, feeding the granules into a fluid-bed reaction zone in which the sulfide material is oxidized at a temperature at least about 20° F. (about 6° to 7° C.) above the softening point of the sulfide and below the melting point of the resultant oxide product in a free O$_2$-containing gas, the oxygen-containing gas being supplied to the roaster at a described fluidizing rate. A method is provided in the process for returning fines to the agglomerator to produce a substantially dust-free oxide product. For example, to produce a "nickel oxide sinter" product consisting of the following procedure was carried out: A pelletized nickel sulfide containing 70% nickel plus cobalt, 25% sulfur, 2.5% copper, and 0.6% iron fed to a fluid-bed reactor at the rate of 3.5 pounds per minute per square foot of roaster hearth was roasted at 2000° F. (about 1090° C.) using an oxidizing gas consisting of 90% air and 10% O$_2$ for forty minutes with no product being discharged during this period. Thereafter, feed was interrupted for 20 minutes while roasting continued for 20 minutes at 2000° F. using the aforementioned oxidizing gas and maintaining roaster temperature at 2000° F. The process can be carried out to produce a final product containing about 1% or less sulfur.

Impurities such as antimony, arsenic, lead and bismuth which are often present in nickel ores and are often considered harmful to catalytic activity can be removed from the nickel material by well-known techniques. For example, they may be removed concurrently with the formation of the precursor material during the fluid-bed roasting treatment.

In the fluid-bed roasting process for obtaining the precursor catalyst material, the roasting is carried out, advantageously, at a temperature in the range of about 600° C. and 1500° C. The fluid-bed roaster provides for good gas-solid contact for the roasting reactions and high gas flows that promote volatilization of impurities and it provides a particle size and structure particularly adaptable to a fluid-bed catalyst reactor. It has been found that fluid-bed roasting at temperatures below about 600° C. produces a material which is less suitable as a catalyst precursor for use in fluidized catalyst bed type reactors.

The process can be carried out to produce a precursor nickel oxide-containing catalyst material having a particle size of at least 0.03 mm. and typically in the range of about 0.25 to about 1.2 mm., with 100% less than 2 ½mm. and a minimum, e.g. less than about 1%, fines.

The nickel oxide-containing precursor catalyst material is treated in an atmosphere reducing to nickel oxide at a temperature of about 200° C. to about 500° C., preferably about 300° C. to about 420° C. or 425° C. to produce a reduced nickel coating on the nickel oxide core with suitable surface characteristics. This can be achieved in a period of time of about ½ to 2 hours. In general, within the given ranges the temperature and time relationship is such that at higher temperatures a shorter period of time is required to obtain a suitable reduced nickel coating having the desired porosity and pore structure. High reduction of oxygen content can be obtained at temperatures higher than about 425° C. (about 800° F.) and shorter periods of time, e.g. ½ hour and less. However, this combination of time and temperature is generally less suitable for developing a suitable pore structure.

Figure 2:
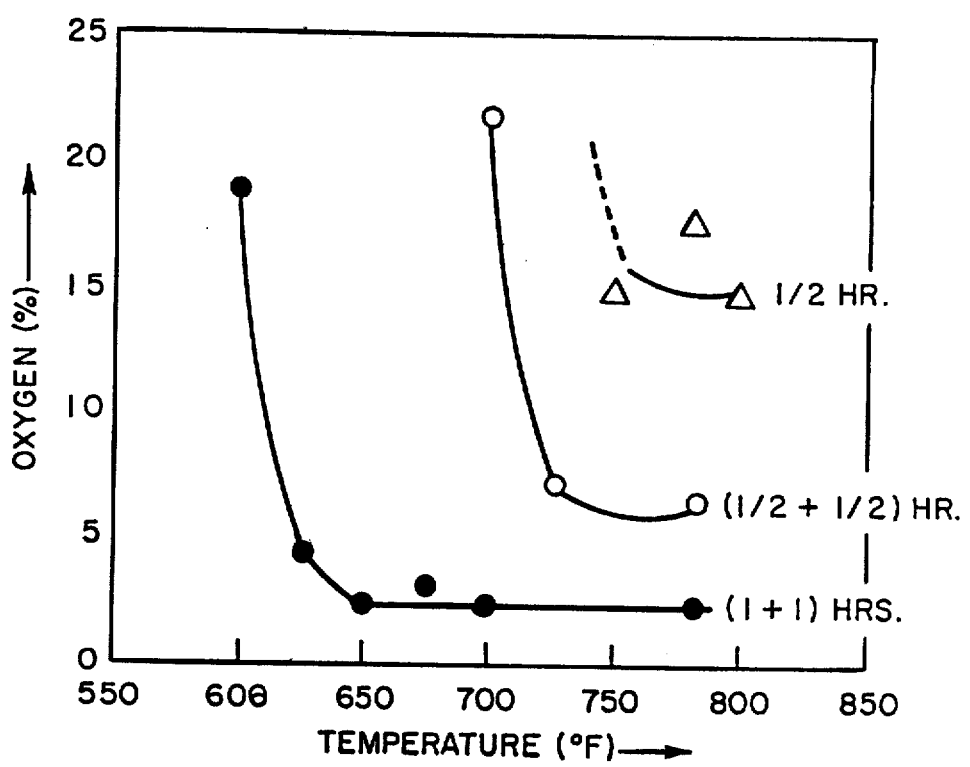
FIGS. 2, 3 and 4 show graphically the effect of various heat treatments on the % $O_2$, surface area and pore volume of a precursor nickel oxide material, respectively.
Figure 4:
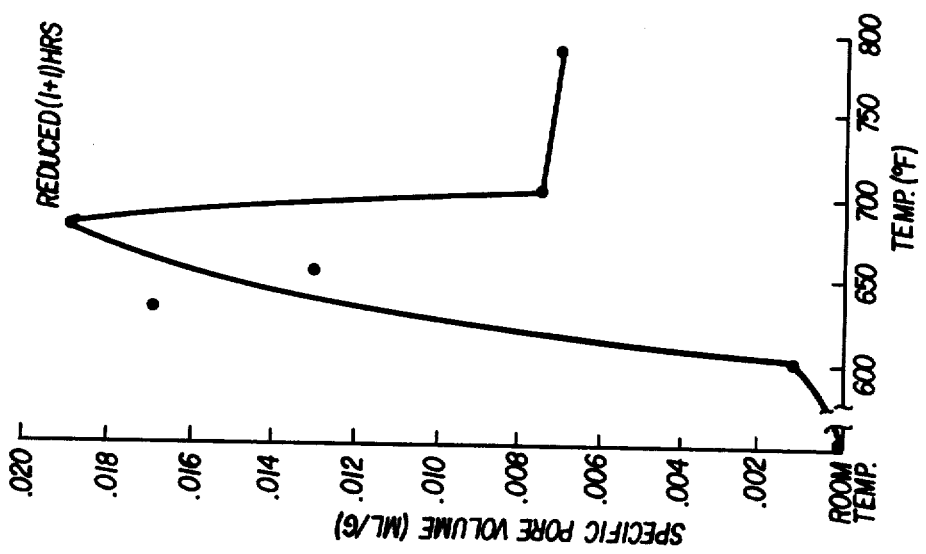
Figure 3:
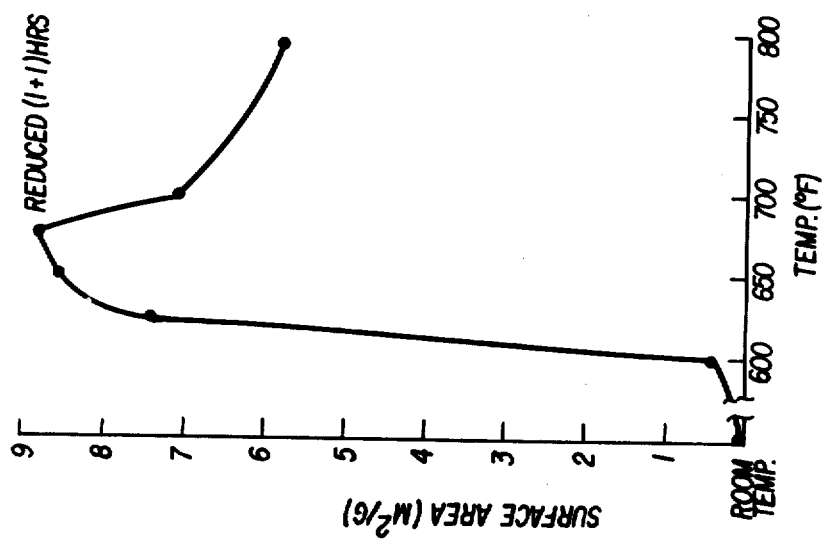

The effect on the nickel oxide-containing precursor material of heat treatment under various conditions of temperature and time with respect to oxygen level, surface area and pore volume is shown in FIGS. 2, 3 and 4, respectively. In general, when the reduction is carried out in the 1+1 hours manner, i.e. with intermediate raking after 1 hour at temperature, the preferred temperature range is about 315° C. to about 420° C., for maximizing the surface area and pore volume. The data in the figures show that within the preferred temperature range catalysts were obtained having an oxygen content of about 19 to 2%, a surface area of about 0.4 to 8.8 m$^2$/g and a pore volume of about 0.001 to 0.02 ml/g. In preferred catalysts the surface area is at least about 3 m$^2$/g and the pore volume at least about 0.01 ml/g. As indicated above, advantageously, the catalyst is reduced in a fluid-bed. This is one method of ensuring that all of the surfaces of the catalyst precursor are exposed to the reducing atmosphere. Another method is to redistribute the catalyst during the reduction treatment. For example, after ½ hour at temperature in the reducing atmosphere the particles are raked or shaken, and then reduction is continued. As indicated above, the precursor material may be reduced on stream and/or prior to use. Cooling is carried out in the reducing atmosphere. Preferably, reduction is carried out to reduce only the surface of the nickel oxide precursor.

The reduced nickel coating formed in this manner is adherent and coherent and, suitably has an average thickness of at least about 1/30 particle diameter and preferably about 1/20 particle diameter to about 1/5 the particle diameter, and it has pore structure characterized by micro-capillaries interconnecting with each other and with the outer surface of the particles. Suitably, the oxygen content of the reduced particles is about 13% or less, e.g. about 7% and preferably it is about 3 to about 13%. For example, a precursor catalyst material having an $O_2$ content of about 26% treated in a reducing atmosphere at about 360° C. (685° F.) for 1 hour followed by raking and further reduction for 1 hour at 360° C. in a reducing atmosphere, produced a catalyst with the following $O_2$ content, surface area and pore volume:
$O_2$ content = 12%
surface area = 8.8 m$^2$/g
specific pore volume = 0.02 ml/g.

The reducing atmosphere is one which is reducing to nickel oxide in the temperature range of the reducing treatment, for example, about 200° C. to about 500° C. The atmosphere may contain, for example, $H_2$, cracked ammonia, a proper reducing mixture of CO and $CO_2$, e.g. a mixture containing 5% to 30% CO and the balance $CO_2$. A free-hydrogen-containing gas, e.g. containing at least 5% $H_2$ in an inert gas such as $N_2$ or Ar, is preferred.

In a preferred embodiment of this invention the particulate unsupported catalyst is used in a catalytic process in a fluidized bed reactor. In general, the reduced catalyst particles are resistant to attrition in the fluidized bed, and reactivation can be achieved simply. In the partially reduced catalyst, the core of the catalyst, is nickel oxide and has a suitable composition and pore structure for development into a reduced nickel of suitable characteristics, hence, if the nickel layer is removed, the core material is further reduced in the reactor to regenerate the reduced nickel coating. If the catalyst is totally reduced, the core is immediately available. This is in contrast to conventional catalysts in which nickel is coated on a ceramic substrate material such as alumina; such catalysts requiring recoating when the nickel is removed from the substrate. If the catalyst is in a fully reduced state the proper pore structure and composition are present throughout for effective catalytic activity.

It is also possible to use the present catalysts in combination with irreducible metal oxides such as oxides of Zr, Ca, Mg, Al, Si, Th and Cr, e.g. up to an amount of less than 25%, preferably less than about 15%. The refractory oxides which may be introduced into the catalyst, e.g. prior to the fluid-bed roasting stage, may serve to stabilize the metallic catalyst phase against loss of area by sintering during the reaction or because of temperature excursions which might occur.

Regeneration of the catalyst can be achieved simply, e.g. by treating the spent or partially spent particles with steam, or in air at a temperature of about 200° to 500° C., preferably up to about 450° C. Reduction conditions are the same as for initial nickel oxide material.

The catalysts of this invention show good activity, selectivity and stability for the methanation reaction. A particular advantage of the present catalysts is that in reduced form prior to and after use the catalyst material is not pyrophoric so that no special precautions need be taken in this regard. A further significant advantage of the present catalyst is that they are stable in the pre-reduced form, thereby making handling of the catalyst more convenient and less costly than pre-reduced nickel catalysts which deactivated at ambient conditions. Another advantage is the catalysts good resistance to poisoning.

The present invention is further illustrated with reference to the examples which follow and the accompanying photomicrographs and graphs.

In the examples the precursor catalyst material used was a nickel oxide sinter product of INCO LIMITED, a particulate material having a nominal particle size of 30 to 85 mesh, formed by fluid-bed roasting a pelleted nickel sulfide at a temperature in the range of about 1100° C. to 1250° C. The material is typically a granular nickel oxide having a nickel content of approximately 76%, a bulk density of approximately 3604 kg/m$^3$ (225 lb/ft$^3$), a surface area of about 0.05 m$^2$/g and a pore volume of less than 0.00002 ml/g. A typical chemical analysis showed, by weight %:

| Ni | Co | Cu | Fe | S | $O_2$ |
|----|----|------|-----|-------|------|
| 76 | 1  | 0.75 | 0.3 | 0.006 | Bal. |

EXAMPLE 1

The purpose of this example is to show the effect of the temperature and time on the pore structure and oxygen content of the nickel oxide precursor material.

Samples (500 gm) of the precursor nickel oxide were carefully reduced and then cooled to room temperature in a hydrogen atmosphere (99.9% $H_2$). The usual procedure was to stir the sample with a rake half way through the treatment cycle to aid in uniform reduction. However, a few tests were carried out without intermediate raking. All tests were carried out between 600° F. (about 315° C.) to 800° F. (about 425° C.) with various periods of treatment, from 30 minutes to 3 hours. Typical results of the tests are summarized in Table I. It was found that both time and temperature affect the degree of reduction and other related properties. Table I gives the effect of time and temperature on the amount of oxygen present, surface area, and specific pore volume of the samples of precursor materials.

Sample X in Table I, for comparison, shows pore characteristics of a reduced particulate nickel prepared from a nickel oxide material comparable to samples shown above, but essentially fully pre-reduced at high temperatures. The preparation of Sample X included a treatment with gaseous chlorine in a fluid-bed reactor at a temperature of about 1200° C. followed by a further fluid-bed hydrogen reduction at a temperature of about 510° C. The nickel product contains about 95% nickel.

In general, it was found that when a hydrogen atmosphere was used, a temperature of at least 325° C. (about 615° F.) is required to lower the nickel oxide to about 15% in 15 minutes time, and to achieve a suitable porosity in the coating.

At higher temperatures, i.e. above 425° C. (about 800° F.) for a total period of time of about 2 hours or more (with intermediate raking), suitably low $O_2$ levels can be achieved. However, the reduction was achieved with some sacrifice in porosity.

Highest values of pore volume and surface area are obtained when the samples are treated at about 350° C. (675° F.) for 1+1 hours (i.e. with intermediate raking). At longer treatment time at temperatures above about 350° C. (675° F.) sintering would start at the surface and value of surface area and pore volume declined, however, the catalyst still showed good performance.

A preferred time/temperature treatment for reduction is at about 315° to 420° C., e.g. about 385° C. (about 725° F.), for a period of about 1 hour with an intermediate raking at about ½ hour, followed by cooling the reduced material, e.g. to room temperature, in the same atmosphere.

Reduction in a fluidized bed is effected within the same temperature and time relationship as the static bed without any special intermediate treatment required.

Figure 5:
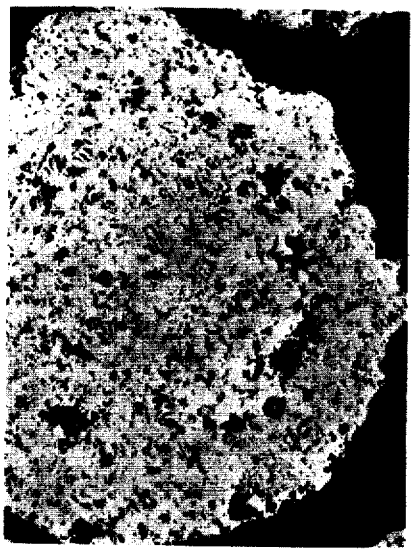
FIG. 5 shows photomicrographs at 200× magnification illustrating the microporosity of a typical material both prior to reduction (5A) and reduced to give a narrow band of reduced nickel in accordance with one aspect of the present invention (5B).
Figure 5:

The photomicrographs in FIG. 5 are a series of micrographs at 200× magnification showing the precursor nickel oxide material (FIG. 5A), i.e. prior to reduction, and after reduction (FIG. 5B), under conditions for Sample C of Table I, i.e. at a temperature of 725° F. (385° C.) for ½+½ hour. FIG. 5A shows a typical micrograph of a nickel oxide-containing precursor material used in the time/temperature reduction tests described above. Typically, the nickel oxide is dark gray in color. White particles indicate reduced nickel. With reduction, a thin band of nickel is produced around the nickel oxide (FIG. 5B). A thicker band indicates greater reduction. Microcapillary connections with each other and the surface are obtained under proper conditions, as shown in FIG. 5B.

Figure 6:
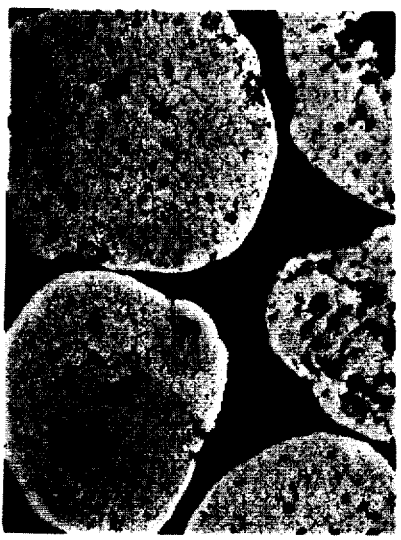
FIGS. 6A and 6B show by photomicrographs at 200× magnification the comparison of a typical microstructure of a catalyst of this invention, prepared from an appropriate precursor and reduced in accordance with the present invention (6A), with a granular reduced nickel product which has not been prepared in accordance with the present invention and does not have the required surface pore structure (6B).
Figure 6:

FIG. 6A is a typical micrograph of the granular nickel (Sample X) reduced at high temperature. In contrast to the catalyst of the present invention fully reduced in use (FIG. 6B), the sample of FIG. 6A has a dense nickel band around the particle.

TABLE I

EFFECTS OF REDUCTION TREATMENT ON PROPERTIES OF CATALYST

| Sample | Temp. (°F.) | Time (hrs.) | $O_2$ Level (%) | Surface Area ($m^2/g$) | Pore Volume (ml/g) |
|---|---|---|---|---|---|
| 0 | As-REceived | | 26.0 | 0.5 | .00002 |
| 1 | 600 | 1 + 1 | 19.0 | .41 | .0014 |
| 2 | 780 | ½ | 18.0 | 1.3 | .0042 |
| 3 | 780 | ½ + ½ | 6.6 | 6.1 | .0073 |
| 4 | 780 | 1 + 1 | 2.5 | 5.8 | .0093 |
| 5 | 700 | 1 + 1 | 2.6 | 7.1 | .0098 |
| 6 | 700 | ½ + ½ | 22.0 | 2.6 | .0102 |
| 7 | 650 | 1 + 1 | 2.5 | 8.6 | .0171 |
| 8 | 800 | ½ | 15.0 | 3.3 | .0157 |
| 9 | 750 | ½ | 15.0 | 4.9 | .0184 |
| 10 | 675 | 1 + 1 | 3.6 | 8.8 | .0250 |
| 11 | 650 | 1½ + 1½ | 3.5 | 6.7 | .0184 |
| 12 | 650 | ¾ + ¾ | 8.2 | 5.1 | .0197 |
| 13 | 650 | ½ + ½ | 7.1 | 5.1 | .0171 |
| 14 | 625 | 1 + 1 | 4.2 | 7.4 | .0223 |
| 15 | 725 | ½ + ½ | 7.3 | 7.6 | .0236 |
| A | 650 | 1 + 1 | 2.6 | 10 | .011 |
| B | 675 | 1 + 1 | 3.6 | 8 | .007 |
| C | 725 | ½ + ½ | 13.0 | 3 | .007 |
| Sample X | As-Received | | 3.3 | 3.3 | .0078 |

EXAMPLE 2

The purpose of this example is to demonstrate the performance of the catalysts of the present invention and to compare such performance with a catalyst not in accordance with the present invention. For the experiment, samples treated as defined in TABLE I for Samples A, B and C, respectively, were subjected to various tests defined as activity, poisoning, sintering tests. Sample D was pre-reduced under conditions comparable to Sample X in TABLE I. Activity was determined before and after sintering. The tests were carried out at an independent laboratory under conditions which simulated a commercial type methanation process. The catalysts were supplied to the independent laboratory in the pre-reduced, stabilized condition, shown in TABLE I.

The procedure to determine catalytic activity is as follows:

2.5 grams of catalyst are charged to the test bed and subjected to a treatment with hydrogen at atmospheric pressure starting at 250° F. (about 120° C.) and heating at a rate of 100° F./hr. (about 38° C. per hour) to 800° F. (about 425° C.) and holding in $H_2$ overnight. The temperature is then dropped to 572° F. (about 300° C.) and the system pressurized with $N_2$ to 800 psi (about 57 Kg/cm$^2$). Thereafter, the feed to the reactor is charged to the methanation feed, consisting of 2% CO, 6$H_2$ and 97% $N_2$. Activity of the catalyst is measured by analyzing the product in a gas chromatograph for $H_2$, $N_2$, $CH_4$, and CO. Several readings are taken over a four hour time span and averaged.

Poisoning resistance of the catalyst is checked as follows: The system pressure is reduced to atmospheric and 3.5 ml of pure $H_2S$ injected from a hypodermic syringe through a serum stopper and flushed through with $N_2$. The system is re-pressurized and the activity checked. Further injections of $H_2S$ to a total of 105 ml are made, with activity checks, to determine the loss in activity with increasing poisoning of the surface.

Sintering of the catalyst is then checked by increasing the temperature to 1300° F. (about 704° C.), followed by re-checking the activity at 572° F. (about 300° C.) Thereafter, the test rig is shut down and the catalyst discharged at room temperature.

Results of the test in tabular form, as reported, are given in TABLE II. TABLE II also gives a comparative test, Run D, using a nickel similar to Sample X and not in accordance with the present invention.

The tests show that in Runs A, B and C, the catalysts were very active for conversion of a synthesis gas to methane. At 300° C., 800 psig, and 28,000 V/H/V (volume of gas per hour per volume of catalyst), the product contained about 75 to 86% $CH_4$ (based on total carbon-containing compounds). Contrastingly, conversion with Sample D (Run D) only 18.2% $CH_4$ was produced. Reference to the poisoning tests in TABLE II show that after a total addition of 105 ml of $H_2S$ the catalyst was still active for conversion of about 41-48% $CH_4$ (at 28,000 hr.$^{-1}$), compared with 15.2% (at 4000 hr.$^{-1}$) for Sample D. Also, it is noted that 70 ml of $H_2S$ is the theoretical amount required to poison all sites on 2.5 gram sample of a commercial catalyst (consisting of tablets of roughly 44-58% Ni on a kieselguhr carrier), which would result in total loss of activity. The results suggest that the present catalyst has good resistance to poisoning. It is believed that poisoning of the catalyst by sulfur occurs by reaction of the sulfur with the nickel. Since the present catalyst contains typically about 75% nickel, it has a greater "sink" for the sulfur than conventional nickel methanation catalysts. This is because there is a greater mass of nickel per unit surface area in the present catalysts.

TABLE II

RUN NO. A CATALYST A (WT. = 2.5066 gm)

(i) ACTIVITY TEST: 300° C.; 800 psig
Carbon containing compounds in outlet gas are: at 28,000 V/H/V

| $CH_4$ | $CO_2$ | CO | Total |
|---|---|---|---|
| 78.8% | 5.6% | 15.6% | 100.0 |

(ii) POISONING TEST: 300° C.; 800 psig
Carbon containing compounds in outlet gas are: at 28,000 V/H/V

| Incremental Addition of $H_2S$ (ml) | $CH_4$ (%) | $CO_2$ (%) | CO (%) | Total (%) |
|---|---|---|---|---|
| 3.5 | 71.1 | 3.5 | 25.4 | 100.0 |
| 7.0 | 68.9 | 3.7 | 27.4 | 100.0 |
| 14.0 | 72.5 | 3.7 | 23.8 | 100.0 |
| 35.0 | 64.6 | 4.5 | 30.9 | 100.0 |
| 70.0 | 54.4 | 4.5 | 41.1 | 100.0 |
| 105.0 | 44.3 | 4.7 | 51.0 | 100.0 |

(iii) SINTERING TEST: 1300° F. (about 700° C.); 500 psig
Carbon containing compounds in outlet gas are: at 28,000 V/H/V

| $CH_4$ | $CO_2$ | CO | Total |
|---|---|---|---|
| 0.8% | 3.2% | 95.8% | 100.0 |

(iv) ACTIVITY TEST (AFTER SINTERING): 300° C.; 800 psig at 28,000 V/H/V

| $CH_4$ | $CO_2$ | CO | Total |
|---|---|---|---|
| 0.0% | 2.5% | 97.5% | 100.0 |

RUN NO. B CATALYST B (WT. = 2.5051 gm)

(i) ACTIVITY TEST: 300° C.; 800 psig
Carbon containing compounds in outlet gas are: at 28,000 V/H/V

| $CH_4$ | $CO_2$ | CO | Total |
|---|---|---|---|
| 75.9% | 4.9% | 19.2% | 100.0 |

(ii) POISONING TEST: 300° C.; 800 psig
Carbon containing compounds in outlet gas are: at 28,000 V/H/V

| Incremental Addition of $H_2S$ (ml) | $CH_4$ (%) | $CO_2$ (%) | CO (%) | Total (%) |
|---|---|---|---|---|
| 3.5 | 82.4 | 5.6 | 12.0 | 100.0 |
| 7.0 | 73.2 | 5.2 | 21.6 | 100.0 |
| 14.0 | 72.2 | 5.0 | 22.8 | 100.0 |
| 35.0 | 63.7 | 4.9 | 31.4 | 100.0 |
| 70.0 | 49.1 | 5.4 | 45.5 | 100.0 |
| 105.0 | 41.7 | 5.7 | 52.6 | 100.0 |

(iii) SINTERING TEST: 1300° F.; 500 psig
Carbon containing compounds in outlet gas are: at 28,000 V/H/V

| $CH_4$ | $CO_2$ | CO | Total |
|---|---|---|---|
| 0.6% | 4.0% | 95.4% | 100.0 |

(iv) ACTIVITY TEST (AFTER SINTERING): 300° C.; 800 psig at 28,000 V/H/V

| $CH_4$ | $CO_2$ | CO | Total |
|---|---|---|---|
| 0.0% | 4% | 96.0% | 100.0 |

RUN NO. C CATALYST C (WT. = 2.5126 gm)

(i) ACTIVITY TEST: 300° C.; 800 psig
Carbon containing compounds in outlet gas are: at 28,000 V/H/V

| $CH_4$ | $CO_2$ | CO | Total |
|---|---|---|---|
| 86.2% | 6.9% | 6.9% | 100.0 |

(ii) POISONING TEST: 300° C.; 800 psig
Carbon containing compounds in outlet gas are: at 28,0000 V/H/V

| Incremental Addition of $H_2S$ (ml) | $CH_4$ (%) | $CO_2$ (%) | CO (%) | Total (%) |
|---|---|---|---|---|
| 3.5 | 73.4 | 6.6 | 20.0 | 100.0 |
| 7.0 | 74.4 | 6.1 | 19.5 | 100.0 |
| 14.0 | 72.7 | 7.0 | 20.3 | 100.0 |
| 35.0 | 68.1 | 6.6 | 25.3 | 100.0 |
| 70.0 | 63.5 | 4.5 | 32.0 | 100.0 |
| 105.0 | 47.7 | 4.2 | 48.1 | 100.0 |

(iii) SINTERING TEST: 1300° F.; 500 psig
Carbon containing compounds in outlet gas are: at 28,000 V/H/V

| $CH_4$ | $CO_2$ | CO | Total |
|---|---|---|---|
| 0.6% | 1.9% | 97.5% | 100.0 |

(iv) ACTIVITY TEST (AFTER SINTERING): 300° C.; 800 psig at 28,000 V/H/V

| $CH_4$ | $CO_2$ | CO | Total |
|---|---|---|---|
| 0.0% | 1.7% | 98.3% | 100.0 |

RUN NO. D CATALYST D (WT. = 2.5073 gm)

(i) ACTIVITY TEST: 300° C.; 800 psig
Carbon containing compounds in outlet gas are: at 28,000 V/H/V

| $CH_4$ | $CO_2$ | CO | Total |
|---|---|---|---|
| 18.2% | 4.5% | 77.3% | 100.0 | at 4,000 V/H/V

| $CH_4$ | $CO_2$ | CO | Total |
|---|---|---|---|
| 35.0% | 5.3% | 59.7% | 100.0 |

(ii) POISONING TEST: 300° C.; 800 psig
Carbon containing compounds in outlet gas are: at 4,000 V/H/V

| Incremental Addition of $H_2S$ (ml) | $CH_4$ (%) | $CO_2$ (%) | CO (%) | Total (%) |
|---|---|---|---|---|
| 3.5 | 31.3 | 4.8 | 63.9 | 100.0 |
| 7.0 | 27.9 | 4.8 | 67.3 | 100.0 |
| 14.0 | 30.9 | 4.8 | 64.3 | 100.0 |
| 35.0 | 29.2 | 4.5 | 66.3 | 100.0 |
| 70.0 | 25.4 | 4.7 | 69.9 | 100.0 |
| 105.0 | 15.2 | 4.4 | 80.4 | 100.0 |

(iii) SINTERING TEST: 1300° F.; 500 psig
Carbon containing compounds in outlet gas are: at 4,000 V/H/V

| $CH_4$ | $CO_2$ | CO | Total |
|---|---|---|---|
| 2.01% | 8.9% | 89.0% | 100.0 |

(iv) ACTIVITY TEST (AFTER SINTERING): 300° C.; 800 psig at 4,000 V/H/V

| $CH_4$ | $CO_2$ | CO | Total |
|---|---|---|---|
| 0.0% | 3.5% | 96.5% | 100.0 |

EXAMPLE 3

The purpose of this example is to illustrate the use of the catalyst in a fluidized bed. The catalyst was supplied to an independent laboratory in a pre-reduced state. Pre-reduction having been carried out at essentially the same conditions is reported in Example 2. No special precautions were taken in delivery or packaging of the catalyst or after use in the reactor.

The test procedure is as follows:

The catalyst is put on-stream without further activation in the following manner. First, cold oil is circulated through the reactor while the system is purged and pressurized with $N_2$, then the system is heated to the reaction temperature. When the system reached operating temperature, the $N_2$ flow is stopped and feed gas (75% $H_2$-25% CO) is metered to the reactor. Steady state conditions are established in a period of several hours (this constituting a run) during which time the process conditions are continuously monitored. Two runs are performed each day on four successive days.

The last run is made after a three-day idle period. At the end of each day the feed gas is changed to pure $H_2$ to react residual CO, and then changed to $N_2$ in order to purge the system. The circulating oil flow is stopped and the reactor is maintained at temperature and pressure overnight.

The results for the process variable scan are presented in TABLE III. The results show that the catalyst of this invention maintained its initial activity level over the entire process variable scan. This is reported to be in contrast to hyperactivity that is typical of "Other commercial methanation catalysts". The maintenance of initial activity level over the entire process variable scan, found with the present catalyst, is believed to be very encouraging when viewed with respect to possible long term catalyst life. The effect of feed gas rate, temperature and pressure were examined and successfully correlated according to the reaction rate model developed by the independent laboratory for their liquid phase methanation process. The activity values are presented in TABLE III. The apparent activation energy, calculated as 15,000–16,000 cal/gm-mole-° K. is as expected for these small size particles. The selectively to $CO_2$, in spite of the stoichiometric $3H_2/1CO$ molar ratio in the feed gas, is a result of the water gas-shift reaction. This occurs because of a measurable water in circulating oil solubility and the high CO partial pressure at the reactor inlet. At very high CO conversions, greater than 98%, the selectively to $CO_2$ again begins to decline, probably due to a reverse shift reaction and subsequent methanation of the CO. This behavior is reported to be typical of all methanation catalysts investigated to date.

sidered to be within the purview and scope of the invention and appended claims.

What is claimed is:

1. An unsupported particulate nickel-containing catalyst material especially useful for methanation reactions composed of, by weight, up to about 13% oxygen, less than about 1% sulfur and the balance predominantly nickel, said catalyst material having an average particle size of about 0.25 to about 1.2 mm. with a minimum of fines, said catalyst particles being a composte material consisting essentially of a nickel oxide core and a thin adherent, coherent layer of nickel on said core, the nickel oxide core having been formed as unsupported nickel oxide particles having an average size of about 0.25 to about 1.2 mm. by fluid-bed roasting and the nickel layer having been developed under reducing conditions from the nickel oxide particles, said nickel layer being characterized by the presence of microcapillary pores interconnecting with each other and with the outer surface of the particles and by a microstructure substantially as shown in FIG. 5B.

2. A catalyst material according to claim 1, wherein the nickel layer has an average thickness of at least about 1/30th the particle diameter.

3. A catalyst material according to claim 1 wherein the catalyst contains up to about 1% cobalt, up to about 3.5% copper, up to about 1.5% iron, up to about 0.1% platinum group metals, and up to a total of about 2% alkali and/or alkaline earth metals.

4. A catalyst material according to claim 1 wherein the catalyst, apart from oxygen and sulfur, contains greater than about 75% nickel.

5. A catalyst material according to claim 1, wherein

TABLE III

Liquid Phase Methanation
Catalyst: Particle size (250–500μ) [1]
Liquid: Witco 40 Mineral Oil
Gas: 75% $H_2$ - 25% CO

| Run No. | Pressure psig | Temp. °F. | Feed Rate, Std. Liters Gas/Hour | CO Conv. % | Hydrocarbon[2] Selectivity % | Apparent[3] Reactivity Act. Units/Gm Cat |
|---|---|---|---|---|---|---|
| 1-1 | 500 | 600 | 675 | 77.5 | 92.6 | 0.44 |
| 1-2 | 500 | 595 | 445 | 87.5 | 91.3 | 0.41 |
| 2-1 | 500 | 600 | 440 | 89.0 | 91.5 | 0.43 |
| 2-2 | 500 | 635 | 485 | 94.9 | 90.8 | 0.64 |
| 3-1 | 500 | 635 | 465 | 95.9 | 91.5 | 0.65 |
| 3-2 | 1000 | 640 | 780 | 97.4 | 93.3 | 0.70 |
| 4-1 | 1000 | 640 | 780 | 97.8 | 93.3 | 0.73 |
| 4-2 | 1000 | 595 | 775 | 89.0 | 93.3 | 0.42 |
| 5-1[4] | 1000 | 635 | 770 | 96.6 | 92.9 | 0.63 |

[1] Catalyst loading = 390 gm ≈130 cm³.
[2] Includes selectivity to $CH_4$ and a small amount of $C_2H_6$. The balance is the selectivity to $CO_2$.
[3] Based on reaction rate model developed by Testing Laboratory.
[4] Reactor not operated for three-day period prior to Run 5-1.

The present invention was illustrated with respect to the use of the catalyst in a methanation reaction to produce synthetic natural gas. Methanation reactions have also been used to purify gas streams, e.g. $H_2$ streams. It is particularly useful for methanation reactions carried out in a fluidized-bed type reactor where the catalyst is. The catalyst of this invention can be used for other reactions, e.g. for hydrogenation reactions, and it is particularly adapted as in the methanation reaction for use in a fluidized bed.

Although the present invention has been described in conjunction with preferred embodiments, it is to be understood that modifications and variations may be resorted to without departing from the spirit and scope of the invention, as those skilled in the art will readily understand. Such modifications and variations are conthe fluid-bed roasted nickel oxide core is an unsupported particulate precursor catalyst material comprising nickel oxide and containing at least about 7% oxygen, less than about 1% sulfur, and the balance predominantly nickel, said precursor catalyst material having a bulk density of less than about 4 g/cc, an average particle size of about 0.25 to about 1.2 mm. with a minimum of fines and said precursor catalyst material on being subjected to reducing conditions being converted to a reduced catalyst material having at least a portion of the nickel oxide reduced at the surface to a thin layer of reduced nickel, said reduced nickel layer being coherent and characterized by the presence of microcapillary pores interconnecting with each other and with the outer surface of the particles and by a microstructure substantially as shown in FIG. 5B and said reduced catalyst material having a superficial surface area of at lest 0.4 m$^2$/g and a pore volume of at least about 0.001 ml/g.

6. A catalyst material according to claim 5, wherein the sulfur content of the precursor catalyst material is a small but effective amount to produce the desired microcapillary pore structure up to about 1%.

7. A catalyst material according to claim 5, wherein the oxygen content of the precursor catalyst material is about 15% to about 26%.

8. A catalyst material according to claim 5, wherein the nickel content of the precursor catalyst material is about 68% to about 93%, and sulfur is present.

9. A catalyst material according to claim 5, wherein the bulk density of the precursor catalyst material is about 2.5 to about 3.6 g/cc.

10. A catalyst material according to claim 5, wherein the precursor catalyst material has an average particle size in the range of about 0.25 to about 0.45 mm.

11. A catalyst material according to claim 7, wherein the oxygen content of the precursor catalyst material is above about 20%.

12. A catalyst material according to claim 8, wherein precursor catalyst material contains up to about 1% cobalt, up to about 3.5% copper, up to about 1.5% iron, up to 0.1% platinum group metal, and up to about 2% alkali and/or alkaline earth metal.

13. A method of preparing an unsupported particulate nickel-containing precursor catalyst material comprising fluid-bed roasting agglomerates comprised of nickel sulfide in an oxidizing atmosphere at a temperature of at least about 600° C. up to about 1500° C. to form directly a particulate precursor catalyst material comprising nickel oxide, said particles containing at least about 7% oxygen.

14. A method according to claim 13, wherein the agglomerates are formed from a nickel-sulfide powder derived from a nickel matte containing at least about 7% sulfur.

15. A method according to claim 13, wherein the particulate precursor catalyst material formed by fluid-bed roasting contains at least 15% oxygen.

16. A method according to claim 13, wherein the particulate precursor catalyst material comprising nickel oxide formed by fluid-bed roasting is treated to form a reduced catalyst material by subjecting said precursor catalyst material to reducing conditions at a temperature of about 200° C. to about 500° C. to convert at least a part of the fluid-bed roasted nickel oxide at the surface of the particles to a thin coherent layer of nickel, said reduced nickel layer being characterized by the presence of microcapillary pores interconnecting with each other and with the outer surface of the particles.

17. A method according to claim 13, wherein the level of fines is less that about 1%.

18. A method according to claim 13, wherein the average particle size is between about 0.25 mm. and about 1.2 mm.

19. A method according to claim 14, wherein the nickel matte contains more than about 15% up to about 26% sulfur.

20. A method of preparing an unsupported particulate nickel-containing catalyst material comprising fluid-bed roasting agglomerates comprised of nickel sulfide in an oxidizing atmosphere at a temperature of at least 600° C. up to about 1500° C. to form directly a particulate precursor catalyst material comprising nickel oxide, said particles containing at least about 7% oxygen, and subjecting said precursor catalyst material to reducing conditions to convert at least a part of the nickel oxide at the surface of the particles to elemental nickel said reduction being carried out in a fluidized bed.

21. A method according to claim 20, wherein the precursor catalyst material is maintained at reducing conditions for a period of time sufficient to lower the oxygen content to about 13% and less.

22. A method according to claim 16 wherein the reduced nickel layer is characterized by the microstructure substantially shown in FIG. 5B.

23. A method according to claim 16, wherein said precursor catalyst material contains a small but effective amount of sulfur to obtain said pore structure in the reduced catalyst material up to about 1% sulfur.

24. A method according to claim 16, wherein said precursor catalyst material contains about 0.02% up to about 0.5% sulfur.

25. A method according to claim 16, wherein the reduced catalyst material has a sulfur content of less than about 0.2%.

26. A method according to claim 16, wherein said precursor catalyst material contains a refractory oxide in a small but effective amount to minimize sintering of the reduced nickel on temperature excursions above the normal operating temperatures for the catalyst, said refractory oxide being introduced into the agglomerates comprising nickel sulfide prior to fluid-bed roasting of said agglomerates.

27. A method according to claim 16 wherein the reduced catalyst material contains, in addition to nickel, at least one element or compound from the groups of the Periodic Table IA, IB, IIA, IIB, IVA, IVB, VB, VIB, VIII, and rare earth metals, and wherein the oxygen content is up to about 13% and the sulfur content is less than about 1%.

28. A method according to claim 16 wherein the precursor catalyst material contains about 68% to about 93% nickel, a small but effective amount to obtain said pore structure up to about 1% sulfur, up to about 1% cobalt, up to about 1.5% iron, up to about 3.5% copper, up to about 2% alkali and/or alkaline earth metals, and up to about 0.1% platinum group metals, said precursor catalyst material having an average particle size of about 0.25 to about 1.2 mm., and said precursor catalyst material on being subjected to reducing conditions, equivalent to a period of about ½ to 2 hours at a temperature of about 315° C. to about 425° C., converting to a reduced catalyst material having an oxygen content of about 19% to about 2%, a sulfur content of less than about 0.2%, a surface area of at least about 0.4 m$^2$/g and a pore volume of at least about 0.001 ml/g.

29. An supported particulate catalyst material prepared by the method of claim 16.

30. A method according to claim 20, wherein the reduction is carried out at a temperature of about 200° C. to about 500° C.

31. A method according to claim 20, wherein the precursor catalyst material is maintained at reducing conditions for a period of time sufficient to lower the oxygen content to about 13% and less.

32. A method according to claim 20 wherein the particulate precursor catalyst material is treated to obtain a reduced material by subjecting the precursor catalyst material to reducing conditions to convert at least a part of the nickel oxide at the surface of the particles to a thin layer of nickel, said reduced nickel being characterized by the presence of microcapillary pores interconnecting with each other and with the outer surface of the particles.

33. A method according to claim 20, wherein said precursor catalyst material contains about 0.02% up to about 0.5% sulfur.

34. A method according to claim 20, wherein the reduced catalyst material has a sulfur content of less than about 0.2%.

35. A method according to claim 20, wherein said precursor catalyst material contains a refractory oxide in a small but effective amount to minimize sintering of the reduced nickel on temperature excursions above the normal operating temperatures for the catalyst, said refractory oxide being introduced into the agglomerates comprising nickel sulfide prior to fluid-bed roasting of said agglomerates.

36. An unsupported particulate catalyst material prepared by the method of claim 20.

37. A method according to claim 32, wherein said precursor catalyst material contains a small but effective amount of sulfur to obtain said pore structure in the reduced catalyst material up to about 1% sulfur.

38. A method according to claim 32 wherein the precursor catalyst material contains about 68% to about 93% nickel, up to about 1% cobalt, up to about 1.5% iron, up to about 3.5% copper, up to about 2% alkali and/or alkaline earth metals, and up to about 0.1% platinum group metals, said precursor catalyst material having an average particle size of about 0.25 to about 1.2 mm., and said precursor on being subjected to reducing conditions, equivalent to a period of about ½ to 2 hours at a temperature of about 315° C. to about 425° C., converting to a reduced catalyst material having an oxygen content of about 19% to about 2%, a sulfur content of less than about 0.2%, a surface area of at least about 0.4 m$^2$/g and a pore volume of at least about 0.001 ml/g.

39. A method according to claim 32, wherein the thin layer of nickel is an adherent, coherent coating having an average thickness of about 1/30th the particle diameter.

40. A method according to claim 35, wherein the refractory oxide is present in an amount of up to about 25%.

41. A method according to claim 35, wherein the refractory oxide is at least one oxide of the metals consisting of zirconium, calcium, magnesium, silicon, aluminum, thorium and chromium.

42. A method according to claim 35 wherein the reduced catalyst material contains, in addition to nickel, at least one element or compound from the groups of the Periodic Table IA, IB, IIA, IIB, IVA, IVB, VB, VIB, VIII, and rare earth metals, and wherein the oxygen content is up to about 13% and the sulfur content is less than about 1%.

43. A method according to claim 22, wherein the thin layer of nickel is an adherent, coherent coating having an average thickness of about 1/30th the particle diameter.

44. A method according to claim 26, wherein the refractory oxide is present in an amount of up to about 25%.

45. A method according to claim 26, wherein the refractory oxide is at least one oxide of the metals consisting of zirconium, calcium, magnesium, silicon, aluminum, thorium and chromium.

* * * * *